United States Patent [19]
Barnard

[11] 4,168,910
[45] Sep. 25, 1979

[54] OPTICAL BEAM-SWITCHING CHOPPER

[75] Inventor: Thomas W. Barnard, Weston, Conn.

[73] Assignee: The Perkin-Elmer Corporation, Norwalk, Conn.

[21] Appl. No.: 900,462

[22] Filed: Apr. 27, 1978

[51] Int. Cl.² .......................... G01J 3/42; G05D 25/00
[52] U.S. Cl. .................................... 356/325; 250/233; 350/285
[58] Field of Search ............... 356/320, 323, 324, 325, 356/326 (U.S. only); 350/274, 285; 250/233

[56]         References Cited
         U.S. PATENT DOCUMENTS 3,901,601   8/1975   Lahmann ........................... 356/325

*Primary Examiner*—Vincent P. McGraw
*Attorney, Agent, or Firm*—S. A. Giarratana; F. L. Masselle; Edwin T. Grimes

[57]           ABSTRACT

An improved optical chopper, developed particularly for use in a double beam atomic absorption spectrophotometer, receives light beams from two separate sources and sequentially switches them into two separate paths and instantly thereafter the second light beam enters the first path, followed immediately by the first beam entering the second output path and then the second beam entering the second path; alternatively, the chopper is arranged so that the first light beam enters the first output path followed by the first light beam entering the second output path, and then the second light beam enters the first path and the second light enters the second path; also, during one segment of the choppers cycle, both beams are blocked from both output paths.

10 Claims, 3 Drawing Figures

OPTICAL BEAM-SWITCHING CHOPPER

CROSS-REFERENCE TO RELATED PATENT APPLICATIONS

The invention described and claimed herein is closely related to copending patent application Ser. No. 819,365, filed July 27, 1977 and assigned to the assignee of the present invention. This copending application is for a reissue of U.S. Pat. No. 3,901,601, which describes and claims an absorption spectrophotometer chopper arrangement which performs the same function as the described and claimed herein but which requires a complex sector mirror and mask combination.

BACKGROUND OF THE INVENTION

The optical beam-switching chopper of the invention is useful in many different optical applications, but was developed particularly for use in a double-beam atomic absorption spectrophotometer which requires the switching of two separate light beams into two separate paths in a particular cyclical sequence so that the detector electronic circuitry can accurately determine an absorption value independently of variations in light beam intensity or detector sensitivity or background absorption that may be caused by molecular absorption or scattering.

In atomic absorption spectrometry, a sample substance is brought into a substantially atomic state, for example, by spraying a solvent containing the element into a flame in the spectrophotometer atomizing furnace. A sample light beam, which originates from a line-emitting light source, such as a hollow cathode tube, and which includes a resonance line of the element to be measured, is directed through the furnace. The desired element in the sample absorbs the resonance lines characteristic of the element and the emerging light beam is directed through a monochromator and thence to a detector which measures the degree to which the desired element absorbs the resonance lines of the sample beam. This absorption degree represents the amount of desired element in the sample substance.

To correct for lamp and detector variations that would obviously cause erroneous measurements, a double beam form the line-emitting source is generally used. One beam passes through the atomic furnace where the element to be measured absorbs its characteristic resonance lines; the other beam, from the same source, bypasses the furnace and is applied directly to the common detector. The ratio of the two signals detected thereby give an indication of the absorption by the element independently of variations in light source or detector sensitivity.

Unfortunately, other error-generating factors exist that cannot be overcome by the above described double-beam system. In practice, other elements in the sample may partially absorb a resonant line and also various components in the burning sample may cause a light scattering. Such scattering and losses due to molecular absorption are designated as "background absorption", and may be measured with a second double beam that originates from a light source having a continuous spectrum, such as a deuterium lamp. This continuous spectrum source follows the same double path and, by comparison of the double path line-emitting beam with the double path continuous spectrum beam, the electronics associated with the detector can readily determine and correct for the background absorption.

This invention is for an efficient optical beam-switching chopper which receives the light beams originating from the continuous spectrum source and from the line-emitting source and, in a cyclical sequence, directs first the resonance line-emitting beam into the atomized sample path, then the continuous source beam into the sample path, followed by the line-emitting beam into the reference path, and then the continuous spectrum beam into the reference path. Alternatively, the chopper is arranged for first directing the resonance line-emitting beam into the atomized sample path and then into the reference path, followed by directing the continuous source beam into the atomized sample path and then into the reference path.

Briefly described, the optical chopper of the invention includes the first rotating chopper disc having two reflecting sectors, each approximately 90° and spaced between open or transparent sectors; and a second rotating disc having four reflecting sectors, each of approximately 45° and spaced between similar open sectors. It is noted that the first rotating chopper disc could have more or less than two reflecting sectors, as long as the second rotating chopper disc has twice as many reflecting sectors as the first rotating chopper disc. The two chopper discs are mounted on a common rotatable shaft and are spaced apart with their reflecting surfaces facing each other. The light beam from a first light source enters the chopper assembly and is folded by a plane mirror between the segmented discs to the reflecting plane of the second or 4-sector disc, while the beam from the second light source is admitted to the chopper at the rear side of the second disc and at a point corresponding to the precise location that the first light source beam strikes the opposite surface. Thus, if there is a reflecting surface at that point, the first light beam will be reflected back toward the first 2-sector disc while the second beam will be absorbed; if there is an open segment, the second light beam will continue toward the 2-sector disc and the first beam will be lost.

The particular beam selected by the position of the 4-sector disc is directed to the reflecting plane of the rotating 2-sector disc. If the beam sees an open section, it passes from the chopper along a first path. If the beam sees an open section, it passes from the chopper along a first path. If the beam strikes a reflecting surface on the 2-sector disc, it is reflected back to a plane mirror which reflects the beam into a second path. Both plane mirrors between the sector discs are positioned with respect to the disc surfaces so as to direct the beams at a favorable angle that optimizes the chopper efficiency.

Alternatively, to change the sequence of operation, the positions of the first and second rotatable chopper discs could be interchanged. Also, in one form of the invention, during one segment of the chopper cycle both beams are blocked from both output paths.

DESCRIPTION OF THE DRAWINGS

In the drawings which illustrate a preferred embodiment of the invention.

DETAILED DESCRIPTION

Although the chopper of the invention may be used in many optical applications, it will be explained in connection with a double-beam atomic absorption spectrophotometer in which a resonant line-emitting light source and a second light beam having a continuous spectrum, are alternately switched between a sample path directed through the absorption cell or sample furnace of the spectrophotometer and a second reference path which bypasses the sample furnace. Both beams are later recombined and eventually directed to a monochromator, detector, and associated electronic circuitry that performs absorption measurements from the detected signals.

Figure 1:
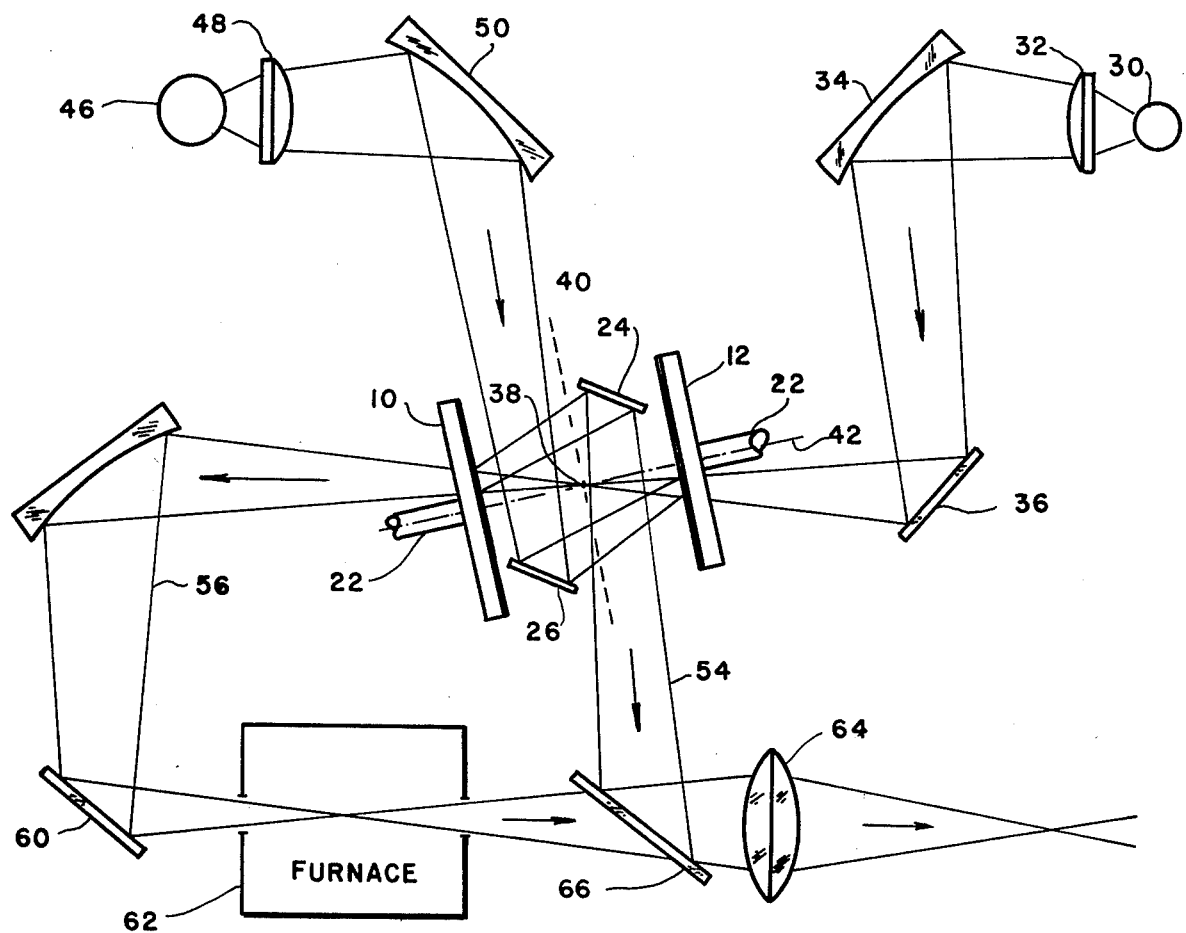
FIG. 1 is a schematic diagram of the chopper of the invention in a typical optical circuit of an atomic absorption spectrophotometer.
Figure 2:
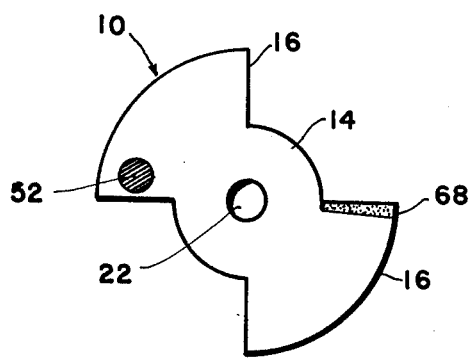
FIG. 2 is a front view of the 2-sector mirror disc of the chopper.
Figure 3:
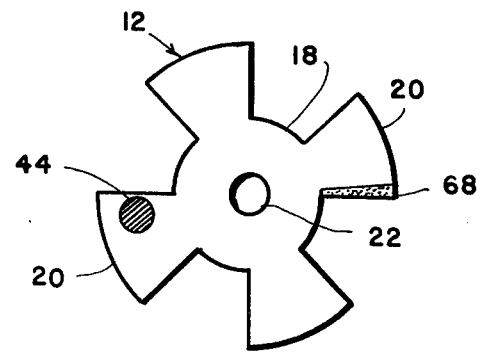
FIG. 3 is a front view of the 4-sector mirror disc of the chopper.

The optical chopper includes a 2-sector reflecting member 10 and a 4-sector reflecting member 12, as best illustrated in FIGS. 2 and 3, respectively. The member 10 includes a central disc 14 that support a pair of blades 16, each having an arcuate width of approximately 90° and spaced between 90° open sectors. Each of the two blades 16 is provided with a mirror surface. Similarly, the member 12 has a central disc 18 that supports four mirrored blades 20, each of which has an arcuate width of approximately 45° spaced between 45° open or transparent sectors. The disc 14 and 18 of the members 10 and 12 are mounted for rotation on a common rotatable shaft 22 and, as illustrated in FIG. 1, are spaced from each other along shaft 22 with their reflecting surfaces facing inward toward each other. As illustrated in FIG. 1, the chopper also includes a pair of plane mirrors 24 and 26 that are statically mounted between the rotating reflecting members 10 and 12.

In the optical circuit of FIG. 1, a resonant line-emitting light source 30, such as a hollow cathode lamp, is positioned so that its light beam is focused by a lens 32, concave mirror 34 and plane mirror 36 to a point 38. The point 38 is on a line formed by a plane, represented by the dashed line 40, that is parallel with and midway between the members 10 and 12 and a second plane 42 that lies along, and is parallel with the rotating shaft 22 of the chopper.

In the preferred embodiment, shaft 22 is inclined at an angle of approximately 13° from the center line of the incoming beam from the source 30. While not essential, this inclined angle facilitates the positioning and the adjustment of the plane mirrors 24 and 26. The beam from the source 30 is therefore directed to the plane of member 12 slightly below the center line shaft 22 and displaced from the side of the shaft as indicated by the cross-hatched disc on the blade 20 of the reflecting member 12 of FIG. 3.

A light source 46 that emits a continuous spectrum, such as a deuterium lamp, is focused by lens 48, concave mirror 50, and folded by the plane mirror 26 against the reflecting surface of the 4-sector member 12. Plane mirror 26 must carefully adjusted so that the center line of the beam from source 46 coincides precisely with the center line of the beam from the light source 30. Furthermore, plane mirror 26 must be carefully adjusted so that the source 46 is also focused on the image point 38; therefore, it is necessary that the incoming beams from source 30 and source 46 follow identical paths between the reflecting surface of the 4-sector member 12 and the image point 38.

The 4-sector reflecting member 12 selects either the light source 30 or light source 46 that is to be imaged at the point 38. If a mirrored blade 20 intercepts the beam from light source 30, the beam from source 46 will be reflected from the mirrored surface to the image point 38. Conversely, if an open space in the member 12 is in a position of the approaching light beams, the beam from source 46 will pass from the chopper and the source 30 will be imaged at point 38.

The 2-sector reflecting member 10 selects the particular output path that the imaged light source at point 38 will take from the chopper. If a mirrored blade 16 intercepts the beam as indicated by the cross-hatched area of FIG. 2, the light source imaged at point 38 will be reflected to the plane mirror 24, which directs the beam to a reference path 54. On the other hand, if an open section between the mirrored blades 16 of member 10 is positioned to receive the beam, it will be directed through a sample path 56 where the image is focused by a concave mirror 58 and plane mirror 60 into the center of the sample atomizing furnace 62 of the absorption spectrometer. The sample beam 56 then emerges from the furnace 62 and is focused by lens 64 to the monochromator and detector. The beam following the reference path 54 is folded by a beam recombiner 66 and, following the same path as sample beam 56, is also focused by mirror 64 to the monochromator and detector.

In a preferred embodiment of the invention, the reflecting members 10 and 12 are 2-sector and 4-sector members, respectively. If desired, the member 10 may have a single reflecting blade of approximately 180° and the member 12 may be a 2-sector member. If desired, the member 10 may have three or more blades, while the member 12 must have twice that number.

Alternatively, to change the sequence of operation, the positions of the chopper discs 10 and 12 could be interchanged, whereby the resonance line-emitting beam 30 is first directed into the atomized sample path 56 and then into the reference path 54, followed by the continuous source beam 46 being directed into the atomized sample path 56 and then into the reference path 54.

The electronic circuitry associated with the detectors of atomizing spectrophotometers generally require a short dark period during which no signal is generated, so that the received signals may be compared in amplitude with a "Zero" input signal. Such a zero input signal may readily be obtained by applying a small beam-absorbing sector, such as the sector 68 of FIG. 3, to the edges of blades 20 to produce a short dark time during which neither the light source 30 nor light source 46 is imaged at the point 38. If desired, a similar dark time absorbing sector may be applied to the transition lines of the reflecting member 10.

Having thus described my invention, what is claimed is:

1. A double beam-switching optical chopper for receiving first and second optical input beams and alternately directing each of said beams into first and second output paths, said chopper including:
a first rotatable disc having at least one reflecting sector and a corresponding transparent sector of substantially equal arcuate length, said reflecting sector and said transparent sector being alternately positioned on said disc;
a second rotatable disc having at least one reflecting sector and a corresponding transparent sector of substantially equal arcuate length, said reflecting sector and said transparent sector being alternately positioned on said disc;

a rotatable shaft coupled to said first and second discs, said shaft maintaining said discs in spaced parallel relationship with facing reflecting sectors;

first optical means for directing the first input beam through the sectors of said second disc and for imaging the source of said first beam at a source image point in a plane substantially midway between said first and second discs;

second optical means for directing said input beam into said chopper and against the plane of said reflecting sectors of said second disc at the point of entry of said first input beam and at a suitable incident angle to said sector plane so that the second beam reflected from said reflecting sectors will be imaged at said source image point;

third optical means for directing the beam at said source image point and reflected from the reflecting surface of said first disc into the first output path; and fourth optical means for directing the beam at said source image point and passed by the transparent sector of said first disc into the second output path.

2. The chopper claimed in claim 1 wherein the first rotatable disc has twice the number of reflecting sectors as the second rotatable disc.

3. The chopper claimed in claim 1 wherein the second rotatable disc has twice the number of reflecting sectors as the first rotatable disc.

4. The chopper claimed in claim 1 or claim 3 wherein said first disc has two reflecting sectors alternately spaced between two corresponding transparent window sectors around the periphery of said disc and said second disc has four reflecting sectors alternately spaced between four corresponding transparent window sectors around the periphery of said second disc.

5. The chopper claimed in claim 1 or claim 3 wherein said second optical means includes a first plane mirror mounted between the parallel reflecting surfaces of said first and second discs.

6. The chopper claimed in claim 5 wherein said third optical means includes a second plane mirror mounted between said parallel reflecting surfaces of said first and second discs.

7. The chopper claimed in claim 1 wherein said chopper is in the optical circuit of an atomic absorption spectrophotometer, said first and second optical input beams are resonant line-emitting beams and continuous spectrum beams, respectively, and said first and second output paths are reference and atomized sample paths, respectively.

8. The chopper claimed in claim 6 wherein said chopper is in the optical circuit of an atomic absorption spectrophotometer, said first and second optical beams are resonant line-emitting beams and continuous spectrum beams, respectively, and said first and second output paths are reference and atomized sample paths, respectively.

9. The chopper claimed in claim 1 or claim 3 wherein the edges of said reflecting sectors of said second disc have beam-absorbing sections for providing dark output signals to the spectrophotometer detector.

10. The chopper claimed in claim 1 or claim 3 wherein the edges of said reflecting sectors of said first disc have small beam-absorbing sections for providing dark output signals to the spectrophotometer detector.

* * * * *